US010888684B2

(12) United States Patent
Nussbaum et al.

(10) Patent No.: US 10,888,684 B2
(45) Date of Patent: Jan. 12, 2021

(54) SLEEP APNEA BALL VALVE DEVICE WITH BLEED FOR EXHALING

(71) Applicant: The Regents of The University of California, Oakland, CA (US)

(72) Inventors: Eliezer Nussbaum, Huntington Beach, CA (US); Carl Kramer, Huntington Beach, CA (US)

(*) Notice: Subject to any disclaimer, the term of this patent is extended or adjusted under 35 U.S.C. 154(b) by 0 days.

(21) Appl. No.: 16/111,091

(22) Filed: Aug. 23, 2018

(65) Prior Publication Data

US 2018/0361108 A1    Dec. 20, 2018

Related U.S. Application Data

(63) Continuation-in-part of application No. 15/960,258, filed on Apr. 23, 2018, which is a continuation-in-part of application No. 15/331,642, filed on Oct. 21, 2016, now Pat. No. 10,751,501, which is a continuation of application No. 14/610,835, filed on Jan. 30, 2015, now abandoned, which is a continuation of application No. 14/465,308, filed on Aug. 21, 2014, now abandoned.

(51) Int. Cl.
*A61M 16/20* (2006.01)
*A61M 16/06* (2006.01)
*A61F 5/56* (2006.01)
*A61F 5/08* (2006.01)
*A61M 15/08* (2006.01)

(52) U.S. Cl.
CPC ............. *A61M 16/208* (2013.01); *A61F 5/08* (2013.01); *A61F 5/56* (2013.01); *A61M 16/0605* (2014.02); *A61M 15/08* (2013.01); *A61M 16/0666* (2013.01); *A61M 16/0683* (2013.01); *A61M 2210/0618* (2013.01)

(58) Field of Classification Search
CPC ................ A61M 16/20; A61M 16/208; A61M 16/0605; A61M 16/0666; A61M 16/0672; A61M 16/06; A61M 15/08; A61M 15/085; A61M 16/0468; A61M 2206/11; A61M 2207/00; A61F 5/56; A61F 5/08; A62B 23/06; Y10T 137/789
USPC ........................... 128/205.24, 206.11, 207.18
See application file for complete search history.

(56) References Cited

U.S. PATENT DOCUMENTS

| | | | |
|---|---|---|---|
| 6,280,166 B1* | 8/2001 | Shiraishi | F04C 29/126 137/533.11 |
| 6,899,127 B1* | 5/2005 | Swingley | F16K 15/04 137/533.11 |
| 9,492,086 B2 | 11/2016 | Ewers et al. | |
| 2009/0194100 A1* | 8/2009 | Minagi | A61F 5/08 128/200.24 |
| 2013/0081637 A1* | 4/2013 | Foley | A61F 5/08 128/848 |

* cited by examiner

*Primary Examiner* — Kendra D Carter
*Assistant Examiner* — Elliot S Ruddie
(74) *Attorney, Agent, or Firm* — Nguyen Tarbet LLC

(57) ABSTRACT

A sleep apnea device with bleed for exhaling including a peripheral wall formed with an interior through passage formed with a proximally facing seat, bleed passages in the wall bypassing the seat and a ball to close against the seat.

12 Claims, 8 Drawing Sheets

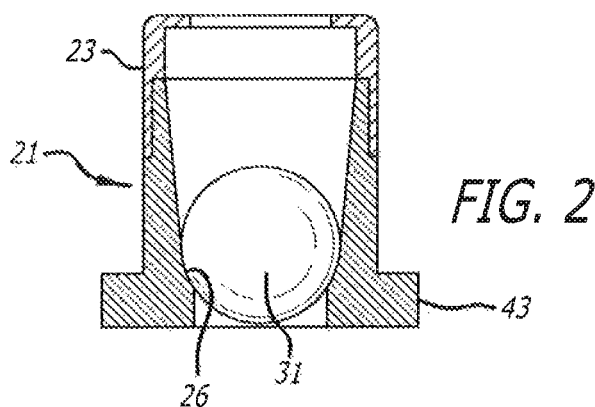
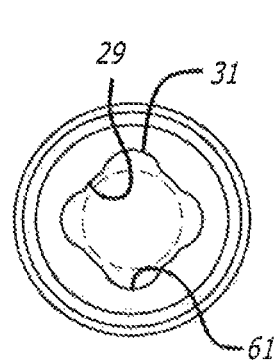
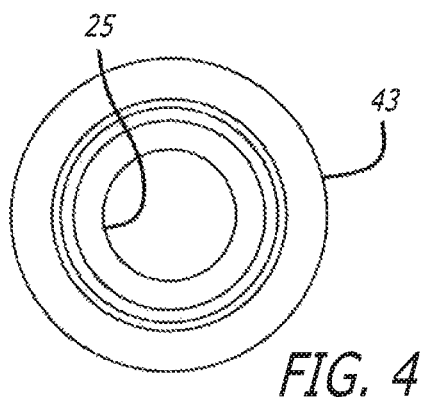
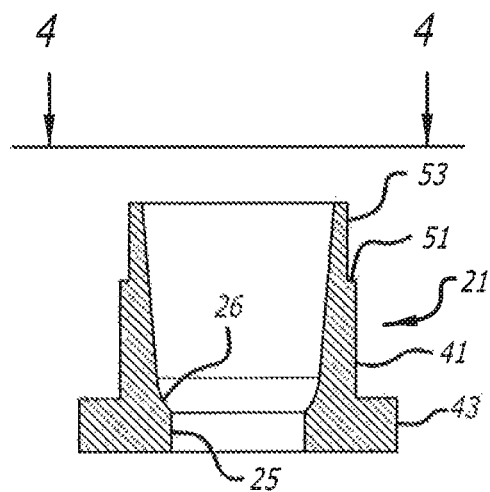
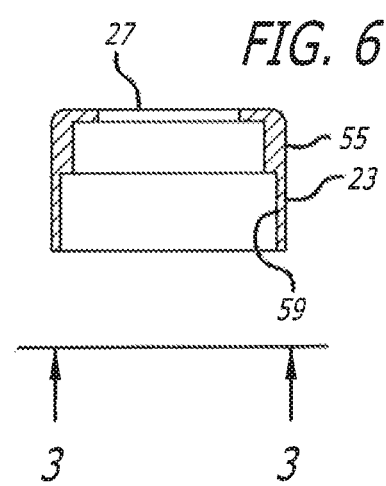

SLEEP APNEA BALL VALVE DEVICE WITH BLEED FOR EXHALING

CROSS-REFERENCE TO RELATED APPLICATIONS

This application is a continuation-in-part of U.S. Ser. No. 15/960,258 filed Apr. 23, 2018, which is a continuation-in-part of U.S. Ser. No. 15/331,642 filed Oct. 21, 2016, which is a continuation of U.S. Ser. No. 14/610,835 filed Jan. 30, 2015, abandoned, which is a continuation-in-part of U.S. Ser. No. 14/465,308 filed Aug. 21, 2014, abandoned, the entire contents of which are incorporated by reference herein and priority is claimed thereto.

BACKGROUND OF THE INVENTION

Field of the Invention

The present invention relates to sleep apnea devices and particularly to the type inserted in the nasal passages to control exhaling by the patient.

DESCRIPTION OF THE RELATED ART

Apnea is a Greek term meaning "without breath." Simply stated apnea means cessation to breathing, something that may lead to decreased oxygen saturation (hypoxia) and an accumulation of carbon dioxide in the bloodstream. Hundreds of millions of patients are afflicted with sleep apnea, a dangerous condition which can lead to sleep deprivation and the consequent unhealthy existence and even death.

There are three types of sleep apnea: Obstructive, Central and mixed. Obstructive sleep apnea is the more common of the two. Obstructive Sleep Apnea can occur as repetitive episodes of complete or partial upper airway blockage during sleep. During an apnea episode, the diaphragm and chest muscles work harder as the pressure increases to open the airway. Breathing frequently resumes with a loud gasp or body jerk. These episodes can interfere with sound sleep, reduce the flow of oxygen to vital organs, and cause heart rhythm irregularities.

In Central Sleep Apnea, the airway is not blocked but the brain fails to signal the muscles to read due to instability in the respiratory center. This affliction is not addressed by the present invention.

Mixed sleep apnea is a combination of both obstructive and central.

While Obstructive Sleep Apnea (OSA) is commonly associated with obesity and the male gender, it affects a broad cross section of the population. Other risk factors include habitual snoring, which is often a precursor of more serious upper respiratory disorders such as Obstructive Sleep Apnea. In fact, results from a recent study indicate that 1 in 3 men and 1 in 5 women who snore habitually suffer from some degree of Obstructive Sleep Apnea.

Symptoms of OSA may be recognized by the bed partner or the patient him or herself. The most common symptoms include snoring, daytime sleepiness or fatigue, restlessness during sleep, sudden awakening with a sensation of gasping or choking, dry mouth or sore throat upon awakening, intellectual impairment, such as trouble concentrating, forgetfulness or irritability, night sweats, sexual dysfunction and headaches.

Left untreated sleep apnea can result in a number of health problems including hypertension, stroke, arrhythmias, cardiomyopathy (enlargement of the muscle tissue of the heart), congenital heart failure, diabetes, and heart attacks. In addition, the untreated sleep apnea may be responsible for job impairment, work related accidents, and motor vehicle crashes as well as academic underachievement in children and adolescents. The risks are significantly increased for those suffering from obesity, chronic lung disease, cardiac disease or COPD.

Obstructive Sleep Apnea Syndrome (OSAS) is a debilitating sleep and breathing disorder which can lead to numerous different afflictions sometimes resulting in stroke, heart attack or other ailments. Debilitating sleep and breathing disorder has been defined as the cessation of breathing for 10 seconds or more (an apnea) at least five times per hour of sleep. Apnea Hypopnea Index (AHI) is the average number of apnea intervals per hour. An AHI of 5 is considered very minimal, less than 15, mild, 30, moderate and over 30, severe.

It is known that the body and muscles relax which can cause excess tissue to collapse into the upper airway (back of the mouth, nose and throat) and block breathing. When breathing is interrupted by an obstruction in the airway, the body reacts by waking enough to start breathing again. These arousals may occur hundreds of times each night but do not fully awaken the patient, who remains unaware of the loud snoring, choking and gasping for air that are typically associated with Obstructive Sleep Apnea Syndrome. Obstructive Sleep Apnea sufferers never get "a good night of sleep" because repeated apneas and arousals deprive patients of REM and deep-stage sleep leading to chronic daytime exhaustion and long-term cardiovascular stress.

Obstructive Sleep Apnea has a profound impact on an individual's health. Excessive daytime sleepiness caused by disruption of normal sleep patterns leads to a significant increase in the rate of accidents for afflicted patients, including a seven fold increase in automobile accidents. Over the long term, Obstructive Sleep Apnea is associated with greater risk of hypertension and cardiovascular disease. The National Commission on Sleep Disorders Research estimates that 3800 cardiovascular deaths due to sleep apnea occur each year. In addition, loud snoring and intermittent breathing interruptions can affect the quality of sleep of the Obstructive Sleep Apnea patient's bed partner. Witnessing an apnea can be a frightening experience because the Obstructive Sleep Apnea patient appears to be suffocating.

According to published data, 24% of adult men and 9% of adult women, or more than 20 million Americans, are estimated to have some degree of Obstructive Sleep Apnea. Of these, six million are estimated to have cases severe enough to warrant immediate therapeutic intervention. However, Obstructive Sleep Apnea was not well understood or recognized by physicians until recently and only a fraction of these 20 million Obstructive Sleep Apnea patients have been diagnosed and treated by a physician. The number of patients currently undergoing treatment is probably on the order of one million.

Hypertension refers to elevated blood pressure and is a common disease, characterized by elevated systolic and/or diastolic blood pressure. Despite the prevalence of hypertension and its associated complications, control of the disease is somewhat inadequate. Only a third of the population suffering with hypertension control their blood pressure adequately. OSA, left untreated can lead to hypertension.

It is known that various forms of positive airway pressure during sleep can provide an effective form of therapy for apnea sufferers. Approaches taken have been to apply Continuous Positive Airway Pressure (CPAP) in which a positive pressure is maintained in the airway throughout the respiratory cycle or Bi Level Positive Airway Pressure (BiPAP) in which positive pressure is maintained during inspiration but reduced during expiration. Intermittent mechanical positive pressure ventilation can be provided where pressure is applied when an episode of apnea is sensed. Positive airway pressure devices have traditionally employed either a face mask to cover the patient's nose or nasal pillows as the interface between a ventilation device and the patient's airways. These interfaces suffer the shortcoming that they are sometimes cumbersome and uncomfortable to wear, often leading to rejection by the patient.

The face mask typically requires a harness, headband or other headgear to hold the mask in position, something patients frequently find uncomfortable, particularly when sleeping. Such face masks are constructed to seal against the patient's face and sometimes chafe against the patient's skin which may cause facial sores, particularly if the patient's sleep pattern involves movement and repositioning during the night. Further, the seal against the patient's face may leak thus reducing or eliminating the efficacy of the device.

Some face mask designs are intended to apply pressure to the sinus areas of the face adjacent the nose, causing the airways to narrow, thereby increasing the velocity of flow through the airway, but decreasing the pressure against the nasal mucosal walls. This process tends to strip moisture from the mucosal wall during inspiration thus drying the wall and producing a burning sensation. Consequently, many patients find the face mask uncomfortable, somewhat ineffective and often results in the patient discontinuing that therapy.

Examples of nasal masks are shown in U.S. Pat. Nos. 5,335,654 and 5,535,739 to Rapoport which describes a CPAP system using a conventional nasal mask.

It has also been proposed to provide nasal pillows which are pressed against the interior portion of the nares to close the nostril openings. Nasal pillows require a robust headband or harness to maintain the pressure thus often leading to discomfort similar to that suffered by use of the face masks.

U.S. Pat. No. 4,782,832 to Trimble discloses nasal pillows held in a patient's nose by a harness arrangement and incorporating two accordion or bellows shaped nipples for fitting against the nostril openings.

It has been recognized that nasal Expiratory Positive Airway Pressure (EPAP) may tend to maintain the patient's airways open during sleep to treat apnea conditions. Different devices have been proposed in effort to provide EPAP, including elongated adhesive strips mounting in the central area a one way valve intended to be placed over the nostrils when retiring. The device is intended to allow the valve to open as a patient inhales but as the patient exhales, close the valve to create a back pressure in hopes of opening the airways to relieve snoring. Such devices, while appearing to offer relief in theory, suffer the shortcoming that the single valve is ineffective to properly control flow through both the patient's nostrils and testing shows that the adhesive strip is challenging to apply and maintain in position during the sleep period.

CPAP is the preferred initial treatment for most people with Obstructive Sleep Apnea. With CPAP, patients wear a mask over the nose and/or mouth. An air-blower forces air into a mask and through the nose and/or mouth. The pressure is adjusted so that it is just enough to prevent the upper airway tissues from collapsing during sleep. The pressure is constant and continuous. CPAP prevents airway closure in use, but apnea episodes return when CPAP is stopped or is used improperly. Patients typically find such masks cumbersome, bulky, uncomfortable, noisy and in need of daily cleaning thus discouraging continuous use.

Other devices have been proposed such as mandibular appliances for patients with mild sleep apnea, dental appliances that prevent the tongue from blocking the throat and/or advance the lower jaw forward. These devices help keep the airway open during sleep.

In effort to avoid the discomfort of CPAP masks, it has also been proposed to provide individual nasal adhesive patches with individual one way valves to be adhered to the patient's nostrils to generate a back pressure upon exhaling. Such devices, while promising in theory, are not adequately affixed to the nostrils in such a manner such as to provide positive lodging in the nasal passage and to positively block flow upon exhaling.

Other efforts to avoid the dreaded CPAP machine proposes an exterior adhesive strip to be applied transversely across the patient's nose and configured with a spring like band to purportedly hold open and extend the nasal passages. Such devices fail to effectively address the issues of sleep apnea.

Chronic Obstructive Pulmonary Disease (COPD) includes chronic bronchitis, emphysema and asthma. In both chronic bronchitis and emphysema, air flow obstruction limits the patient's airflow during exhalation. COPD is a progressive disease characterized by a worsening base line respiratory status over the period of many years with sporadic exacerbations often requiring hospitalization. Early symptoms include increased sputum production and sporadic acute exacerbations characterized by increased cough, purulent sputum, wheezing and fever. Late in the course of the disease, the patient may develop hypercapnia, hypoxemia, cor pulmonale with right-sided heart failure and edema.

Pulmonary rehabilitation is frequently used to treat patients suffering from a variety of medical ailments such as those mentioned. For example, COPD patients are taught new breathing techniques that reduce hyperinflation of the lungs and relive expiratory airflow obstructions. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. It is believed that producing a proximal obstruction (e.g. pursing the lips) splits open the distal airways that have lost their tethering in certain diseased states.

It has been reported that pursed-lip breathing by COPD patients results in a reduction in respiratory rate and an increase in tidal volumes and an improvement of oxygen saturation. However, pursed-lip breathing requires conscious effort, thus the patient cannot breathe through the pursed lips while sleeping. As a result, the patient can still become hypoxic at night and may develop pulmonary hypertension and other sequelae as a result.

Non-invasive Positive Pressure Ventilation (NPPV) is another method of treating diseases that benefit from regulation of the patient's respiration. NPPV refers to ventilation delivered by a mask, nasal prongs, pillows or face mask. NPPV eliminates the need for intubation or tracheostomy.

NPPV can deliver a set pressure during each respiratory cycle, with the possibility of additional inspiratory pressure support in the case of bi-level devices. It is recognized that most patients experience difficulty adapting to nocturnal NPPV leading to poor compliance. Mask discomfort is a very common problem for patients new to NPPV, because the high pressure om the nose, mouth and face and because the tight straps are uncomfortable.

Both the pursed-lip breathing and the use of NPPV have been shown to offer significant clinical benefits to patients with a variety of medical illnesses including COPD, heart failure, pulmonary edema, sleep apnea and other sleep breathing disorders. Expiratory resistance is believed to provide the bulk of clinical improvements when using pursed-lip breathing and NPPV, through a variety of physiological mechanisms. For example, in COPD expiratory resistance is believed to facilitate expiration, increase tidal volume and decreases respiratory rate. Various devices have been proposed for applying positive pressure to the patient's nostrils and even for balancing flow between the two nostrils. See U.S. Pat. No. 5,740,799 to Nielsen.

It has been proposed to extend the expiratory time in effort to reduce the respiratory rate as by incorporating a flap valve in a nasal device for restricting exhalation flow and facilitating connection to an oxygen source. A device of this type is shown in U.S. Pat. No. 7,856,979 to Doshi. Such flap valves have not proven satisfactory for these applications.

Many different configurations of CPAP devices have been proposed, including face mask, nasal prongs and nasal cannulas, each having advantages and disadvantages. One objective of the art has been to devise a comfortable nasal cannula which is economical to manufacture and practical to use. Prior art nasal cannulas have been disclosed in many forms with various methods of securing the device to the nasal passageway. One such cannula assembly is disclosed in U.S. Pat. No. 3,513,844 utilizing an adjustable strap to encircle the individual's head. A similar device is disclosed in U.S. Pat. No. 4,106,505 wherein the supply tubes to the cannula are hooked over an individual's ears and around the head. Even more cumbersome is the device disclosed in U.S. Pat. No. 5,477,852 incorporating a headband for holding and positioning the nasal inserts and associated supply tubes. Yet another system in U.S. Pat. No. 5,271,391 discloses a cannula which is secured by applying strips of pressure sensitive adhesive tape to the supply tubes leading from each side of the cannula, thereby attaching the supply tubes to the cheeks of an individual with a cannula positioned in between. These head harness devices are commonly found necessary to hold the CPAP prongs in place.

Other efforts have led to a proposal of CPAP devices for treatment of sleep apnea with relatively stiff or rigid nasal cannula surrounded by inflatable cuffs to retain the cannula in the pares as shown in U.S. Pat. Nos. 5,269,296; 5,477,852 and 5,687,715 to Landis. It has also been proposed to telescope a soft ring-shaped flange over a cannula as shown in U.S. Patent Publication No. 2009/0032208 to Bare to assist in retaining the cannula in the patient's mask.

However, these prior methods, are in some cases, rather complicated and expensive to manufacture and in the other cases, ineffective to secure the cannula in place without cumbersome head gear. Some apply pressure to an individual's nose and upper lip thereby causing pressure necrosis in the upper center of the nose. Many of the head harnesses fail to adequately secure the prongs in position, particularly with infants or patients who tend to roll around or move during the sleep phase. The discomfort of head harnesses and the like can often lead to the patient intentionally or unintentionally removing the harness and disconnecting the device thereby leading to sleep apnea, distractions, bradycardia, or hypoxia which is known as a dangerously low oxygen level in the blood. In practice, the tubing for many of these head harness devices is typically draped around both sides of the patient's cheek which means that the most comfortable lying position is on the patient's back thus producing a tendency to snore and create a uncomfortable sleeping position for the patient.

Other efforts to develop satisfactory anchoring systems include adhesive devices which attach directly to the nose. U.S. Pat. No. 4,823,789 discloses a nose tube anchoring strip which has an adhesive coated strip to fit over the individual's nose and an appendage for holding a nasal-gastric tube in place. A similar device is found in U.S. Pat. No. 5,156,641 disclosing an anchoring cord adhesively attached to an individual's nose at one end and attached to hold the naso-gastric catheter at the other end. U.S. Pat. No. 5,138,635 shows an anchoring device with a body engagement portion which adheres across the nose of an individual with cannula engaging portions extending downwardly.

One of the challenges facing artisans in seeking to develop a satisfactory apnea device is, to provide a device which affords adequate air flow while avoiding the necessity of applying uncomfortable head harnesses, masks and the like to hold the device in place within the nasal passages. A particular problem is the discomfort associated with the use of such devices. That is, the artisan is faced with the dilemma that a nasal device must be of sufficient structural integrity to maintain a flow passage sufficiently opened as to afford a high rate of flow during an expiration while, at the same time, providing comfort within the nasal passage. As will be recognized abrupt changes in cross sectional shape of the cannula device, as such as presented by the end of a rigid wall will, over time, create irritation within the soft tissues of the nasal passage thereby discouraging continuous use and even resulting in an unconscious desire by the patient to involuntarily remove the device during the sleep period. Until now the artisan has been faced with the dilemma of sacrificing rigidity in the cannula to achieve comfort of seeking to devise a cannula with varying rigidity.

This issue of discomfort in the nasal passages has plagued the art for some time. Numerous different approaches have been taken in effort to solve the dilemma of anchoring the nasal devices in place in a manner which will not excessively contribute to the patient's discomfort while providing a robust flow passage.

As an example, U.S. Pat. No. 4,823,789 discloses an adhesive device to attach directly to the nose via an adhesive coated sheet including an appendage for holding the nasogastric tube. In this regard, it has been proposed to provide sponge-like nasal tips which are manually compressible to reduce the size for convenience of insertion and having a relatively slow rate of expansion seeking to block the nasal passage. A device of this type is shown in U.S. Pat. No. 4,648,398 to Agdenowski. Devices of this type, while having a sealing capability are relatively cumbersome and fail to address the issue of high rates of flow in the flow passage.

Other efforts have led to the proposal that a nasal buff be provided with external nasal sealing means which incorporate pliable, conical nare pillows to be constructed of rigid, synthetic resin material and include a bellows arrangement for accommodating the various orientations of the nasal passage or a nasal pillow constructed of a soft resin such as cell foam or gel filled with silicone. Such devices, while providing some comfort in accessing the orifici at the distal extremity of the nasal passages, fail to address the complications relating to high flow rate and convenient retention in the nasal passages without complicated tubing and headgear.

Other proposals have been made for a tubing system to surround the user's head or neck and carrying a crescent shaped tube device in the frontal area with upwardly projecting tubes for telescopically receiving tubular nasal elements formed at their proximal extremities with enlarged rims. A device of this type is shown in U.S. Pat. No. 6,478,026 to Wood. Such devices incorporate relatively complicated valve systems and, furthermore, are cumbersome to use and can readily generate discomfort in the nasal passages due to the misalignment between the orientation of the patient's nasal passages and the device itself.

It has also been proposed in the unrelated art of medicine that inhalers incorporate a nasal interface tube with left and right nasal prongs that pinch the nasal septum in order to retain the device in place. A device of this type is shown in U.S. Patent Application Publication No. 2002/0046751.

In recognition of shortcomings of the interface with the patient's nostrils and sealing capabilities, it has been proposed to provide a harness mounting nasal tubes at the interface with various fittings which abut or only slightly penetrate the nasal passage. A device of this type is shown in U.S. Pat. No. 8,136,527 to Wondka. These devices are also relatively cumbersome in that the harness typically involves a connection about the patient's ears or around his or her neck and little attention is given to the sealing characteristics of the peripheral of the nasal devices with the nasal tissues or any consideration to possible discomfort deep in the nasal passages.

Other devices, such as ball valves have been proposed in unrelated art for interrupting oxygen supply during the patient's exhale phase. A device of this type is shown in U.S. Patent Application Publication No. 2008/0142012 to Farnsworth.

It has been recognized that debris can build up in a valve arrangement of a face mask and that the consequent pressure build up can be relieved through a side vent of a control valve and an anti-asphyxia bypass feature. A device of this type is shown in U.S. Pat. No. 7,559,326 to Smith. Devices of this type, while tending to serve their intended purpose, suffer the shortcoming that some patients resist use of a mask covering a portion of the patient's face and the fact that failure to totally block exhalation fails to afford effective relief from a patient suffering from sleep apnea.

It has been proposed to restrict flow during the exhaling phase as in U.S. Patent Publication No. 2013/0081637, now U.S. Pat. No. 9,730,830 to Foley, while providing for robust bleeding of air outside the valve to give the patient a feeling of comfort in breathing. Such devices and their methods of use do not provide the benefits associated with highly restricted flow during the exhaling phase. As will be appreciated, while Foley seeks to provide for bleeding through the valve poppet or diaphragm, his construction is extremely complicated and intrusive. His valve projects distance beyond the valve seat and expands radially outwardly to such an extent as to render proper operation in the close confines of the nasal passage highly questionable. In fact, it would appear that a physical embodiment of such a device would be so heavy, large and cumbersome as to require radial engagement to hold the device in the nasal vestibule.

It has been proposed to provide a flapper-type valve or duck-billed valve to limit the rate at which air may be exhaled. It has been proposed to provide a flap-type valve to restrict airflow to configure the flap such that in the closed position, air can flow through an opening in the flap. A device of this type is shown in U.S. patent application Ser. No. 12/711,781 to Doshi, now U.S. Pat. No. 7,992,564.

There thus remains a need for a device of this type which is convenient for a patient to apply and which will effectively restrict flow on exhaling to bypass the valve so as to avoid giving the patient the sense of suffocating.

SUMMARY OF THE INVENTION

In one aspect, the present invention includes a nasal valve device formed by a housing constructed of a distal tube and proximal cap joined together to form a through-passage and configured on the interior with a proximally facing seat and on its proximal end with radially inward projecting stops to limit proximal travel of a rounded poppet held captive in the passage for oscillating off the seat during the inhaling cycle and nesting on the seat during the exhaling cycle to positively block air flow past the seat. The housing includes a bleed passage bypassing the seat to allow for a limited volume of exhalation.

The features and advantages of the invention will be more readily understood from the following description which should be read in conjunction with the accompanying drawings.

BRIEF DESCRIPTION OF THE DRAWINGS

FIG. 2 is a vertical sectional view of one of the nasal housings included in the device shown in FIG. 1;

FIG. 3 is a transverse view taken along the line 3-3 of FIG. 6;

FIG. 4 is transverse top view taken along line 4-4 of FIG. 5;

FIG. 5 is a vertical sectional view of a housing incorporated in the device shown in FIG. 1;

FIG. 6 is a detailed sectional view of a cap incorporated in our invention shown in FIG. 1;

DETAILED DESCRIPTION OF THE PREFERRED EMBODIMENTS

Figure 1:
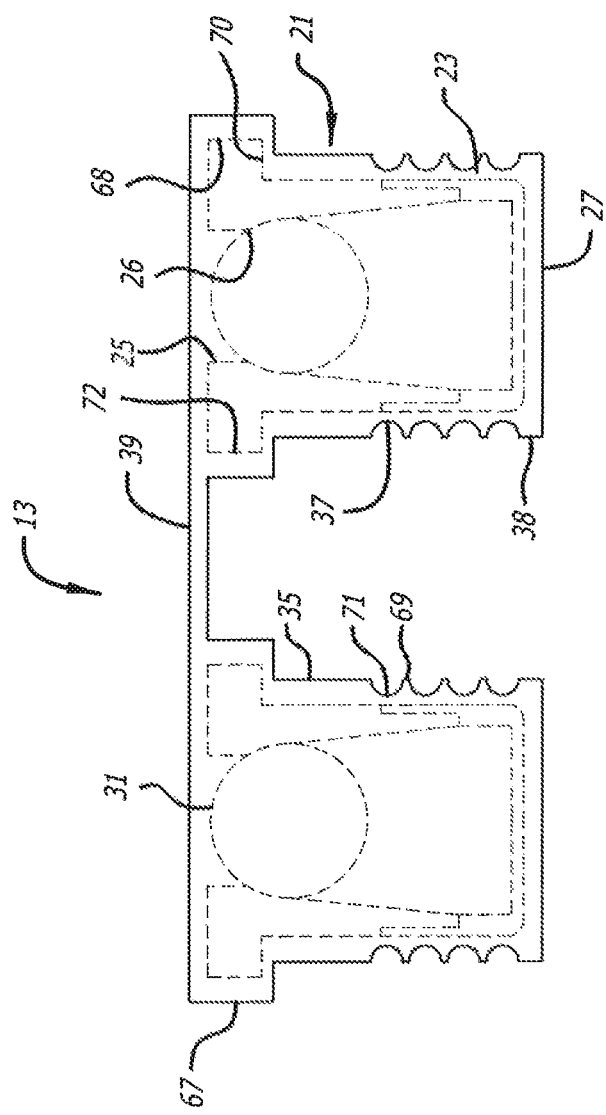
FIG. 1 is a front view of a sleep apnea device related to our present invention, inverted in the interest of clarity.

Referring to FIGS. 1 and 2, one version of our sleep apnea nasal device includes a pair of housings formed by relatively rigid tubular bodies 21 cooperating to form through passages 49 having distally disposed, proximally facing valve seats 26. The bodies are capped on their one extremities with respective caps 23 and configured on their distal ends with respective reduced-in-diameter inlets 25. The caps 23 are formed at their proximal ends with respective outlets 27 having a plurality of radially inwardly projecting lobes spaced equidistant thereabout to be formed at their radially inner extremities with distally facing stops 29 (FIG. 3) and cooperating at their radially inner ends to combine in forming an opening having a diameter smaller than that of a valve ball defining a rounded poppet 31 held captive in the housings. A harness device, generally designated 33, is formed of pliable elastic material configured to form respective expandable barrels 35 and 37 to be received telescopically over the respective housings and includes a nasal strap 39 connecting the most distal ends thereof together. Thus, in operation, the device is constructed of a minimal number of parts, economical to manufacture and assemble, and comfortable to use in providing for positive blocking of flow during the patient's exhaling cycle.

Figure 12:
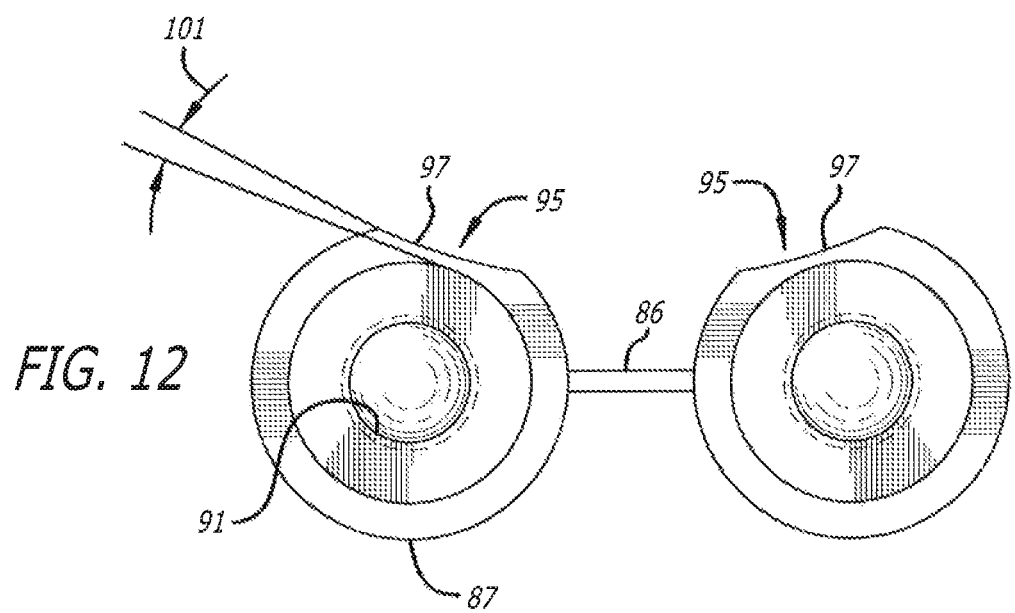
FIG. 12 is a top view, in enlarged scale, of the device shown in FIG. 11.

For the purposes of this disclosure, we sometimes refer to the device as if the tubular bodies and caps were inserted in the patient's nasal passages as shown in FIG. 12 to define proximal and distal extremities. We also sometimes refer to the bodies as being cylindrically shaped, terms that are intended to mean a transverse direction, whether a classic cylindrical shape or transversally elongated as will often be the case for an elliptical configuration.

Figure 9:
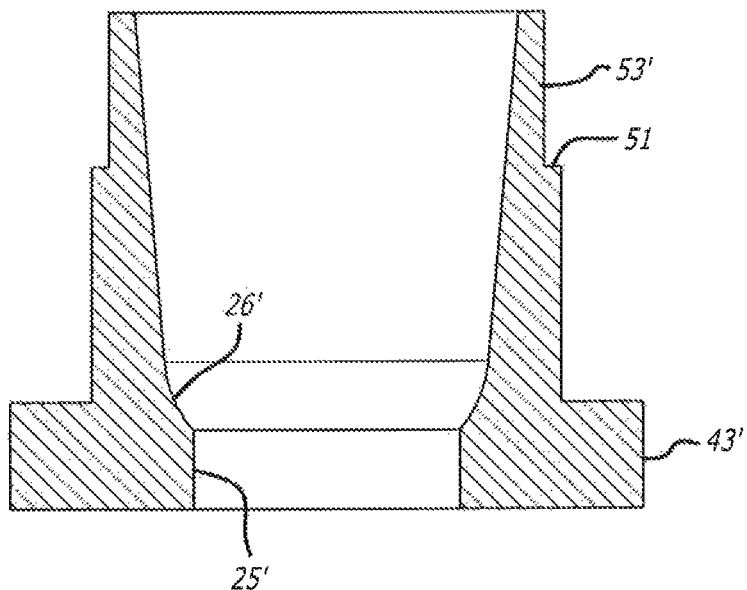

Referring to FIGS. 5 and 9, bodies 21 may be formed with cylindrical tubes 41 configured on their proximal end with a radially outwardly projecting annular flanges 43 and interiorly with the reduced-in-diameter inlets 25. The interior walls of the barrels taper distally inwardly at an angle of 10 degrees to their axes to cooperate in forming the conical interior passages 49. The barrel tubes are configured at the inlets 25 with the proximally facing integral conical valve seats 26 curving radially inwardly and distally at a radius of curvature corresponding with the curvature of the surface of the rounded poppet to cooperate with the respective walls to form respective annuli having radial dimensions dictated by the distance to which the respective poppets are drawn off the seat and to, when the poppet is driven there against, cooperate to form positive seals against distal escape of air. The exterior of the barrels 41 are stepped down on their proximal extremities to form proximally facing shoulders 51 at the respective one ends of proximal male glands 53 (FIG. 5).

Figure 7:
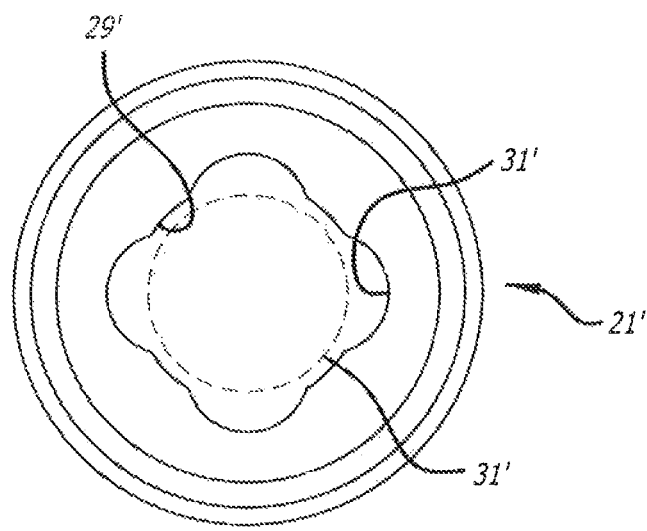
FIGS. 7, 8, 9 and 10 are views similar to FIGS. 3, 4, 5 and 6, respectively, of a second embodiment of the device shown in FIG. 1.
Figure 8:
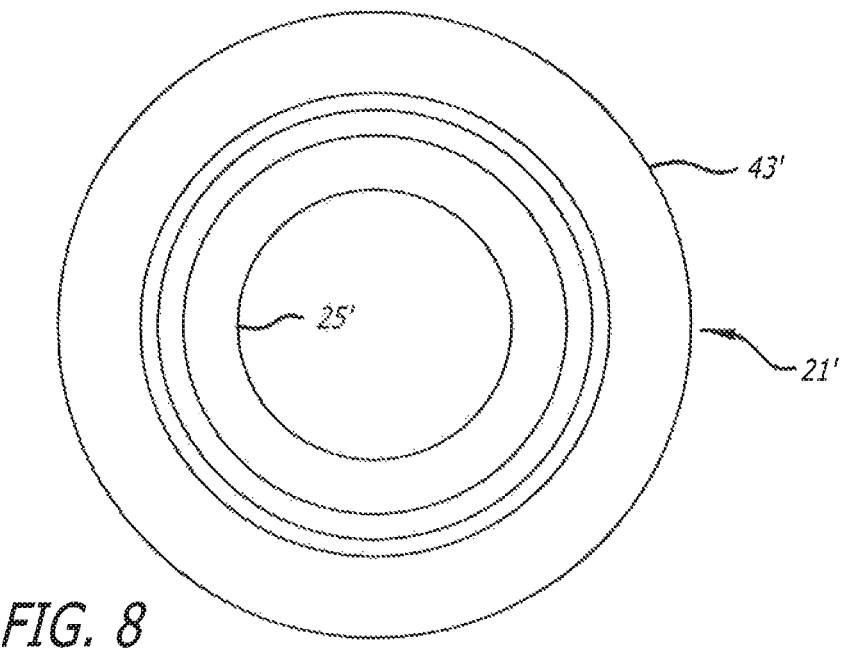

Referring to FIGS. 2-5, the flanges are constructed to provide enlarged diameters for the patient to conveniently grasp by his or her fingers to facilitate insertion and removal, and to also to, when inserted, overlie the exterior surface at the ends of the respective nostrils to cooperate in blocking an air flow around the exteriors of the housings. To that end, we construct the sizes of the housings and flanges to complement the anatomy of the particular patient. For patients of a smaller anatomy (children and young adults), we construct the devices with the smaller cross sections as shown in FIGS. 1-6, and for adults, larger cross sections as shown in FIGS. 7 and 8.

Figure 10:
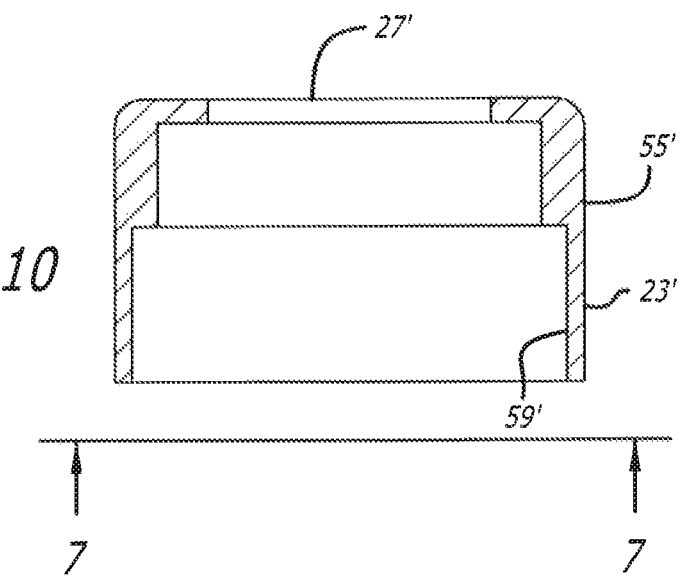
Figure 11:
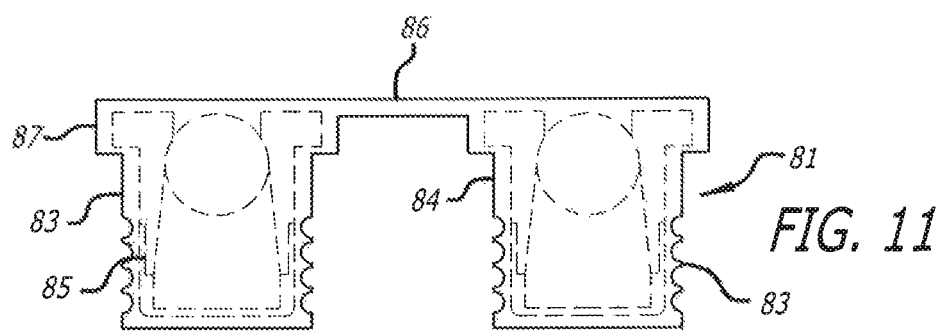
FIG. 11 is a front view of a further embodiment of the harness incorporated in the present invention.

Referring to FIGS. 6 and 10, the caps 23 are cup-shaped to form distally projecting cylindrical walls 55 configured with an interior chambers 57 having increased-in-diameter female glands 59 to complementally fit in telescopical relationship over the male glands 53.

The caps 23 are formed at the inlets with the radially inwardly projecting stops 29 which may be in the form of radial prongs, lobes or spokes constructed so the radially inward extent thereof cooperate in forming a loci defining a circle having a diameter smaller than that of the ball poppets 31. The lobes defining the stops terminate in radially outwardly concave arcuate radially inwardly facing edges having radii of curvature complementing the radius of the ball poppet at the diameter of contact when the poppet is fully open. The stops cooperate to form there between, at their root sections semicircular surfaces 60 cooperating with the poppets to define bypasses 61 (FIGS. 3 and 7) for bypass of air out the inlets 27 when the patient is exhaling. In one preferred embodiment the outlet may be shaped so the bypasses cooperate to, in end plan view, exhibit the shape of a four leaf clover.

Referring to FIGS. 2 and 3, the poppets 31 are in the form of lightweight rounded solid or hollow bodies having rounded peripheral surfaces to be complemented on one side by the shape of the seats 26 and to cause the surfaces in the four quadrants nest against the respective distally facing tips of the stops 29 to cooperate in forming the respective bypasses 61 spaced equidistant about the outlet. Thus, during the inhalation cycle as the pressure differential tends to lift the poppets 31 off the respective seats 26, air flow will commence in the crescent shaped bypasses 61 at the four quadrants to cause the air flow past side poppets to apply a balanced drag to such four quadrants of the poppets to lift them centrally in the respective passages causing air entering through the inlet 25 to be distributed in respective longitudinal flow paths up around the poppets to lift the poppets a greater distance off the respective seats 26 proportional to the rate of air flow to direct such air in four substantially equal volume flow streams spaced equidistant about the equator of the poppet and out the inlets 25 into the patient's nostrils.

In one preferred embodiment the poppets are in the form of balls defining spheres having surfaces with the same radius of curvature as that for the axial radius of curvature for the seat 26. In some embodiments the poppets may be elongated in the axial direction of the passages to take an elliptical shape with the y axis having a diameter greater than the transverse inside diameter 28 of the seats 26. In one preferred embodiment, the spherical poppets are formed by a thin skin defining a hollow construction to present a lightweight feather-like mass weighing less than 0.010 grams, preferably between 0.0010 and 0.010 grams to present minimal resistance to being lifted off the seat 26 by the pressure differential generated thereacross and air flow drag as the patient inhales. We have demonstrated that the poppet may be constructed of ceramic, silicone or other medical grade material.

The harness device 33 is formed of known pliable, elastic elastomeric materials. The harness acts a sheath device and includes the respective sheath barrels 35 and 37 constructed of relaxed unstretched inside diameters slightly less than the outside diameters of the respective housing bodies 21 to be stretched thereover to grip and hold the housing bodies frictionally in place. In practice, we have constructed the sheath barrels 35 and 37 with the relaxed unstretched interior diameter approximately 10% smaller than the outside diameter of the housing barrels.

The sheath barrels 35 and 37 are configured at their distal ends with respective diametrically enlarged sheath rims 67 formed with annular walls 68 rising from bottom walls defining respective walls 72. The bottom walls 70 of the well act as stops to limit the distance the barrels can be drawn distally on the housing. The connector strap 39 is connected on opposite ends to the most distal extremities on the proximal sides of the respective rims 67. In a preferred embodiment the ends of the body of the strap 39 are connected at the most distal point of the respective barrels so the body of the strap is located in a distal plane such that it is disposed in the distal one quarter of the flanges so as to provide maximum clearance from the distal end of the nose on insertion. The sheath barrels are conveniently formed along their exterior longitudinal diameter with annular, axially spaced apart ribs 69 to form therebetween annular grooves 71 to define a somewhat corrugated longitudinal surface for interfitting the interior surface of the nasal passages to perform a gripping function to hold the device in place. In some embodiments we form the sheath barrels 35 and 37 longer than the bodies 21 to, when the flanges are nested in the ribs, project proximally a short distance beyond the proximal ends thereof to form a pliable, annular cushion. We have found that constructing the barrels of a length to form the cushion 38 of a length of between 1/32 of and 3/8 of an inch works well, and preferably between 1/16 and 1/8 of an inch.

In operation, it will be appreciated that the respective housing bodies 21 and caps 23 may be injection molded from thermoplastic to the described configuration. Assembly will thus merely involve capturing the poppet 31 in the chambers 57 as the parts are brought together and adhered by a known commercial process. The ball poppet will thus be held captive to oscillate within the respective chambers trapped at one end by the lobes defining the stops and on the other by the annular seat 26.

The assembled housing devices may then be inserted in the sheath barrels 35 and 37 to be held frictionally in position for use by the patient with the cushions leading the way and providing cushioning for the proximal ends of the bodies.

Figure 13:
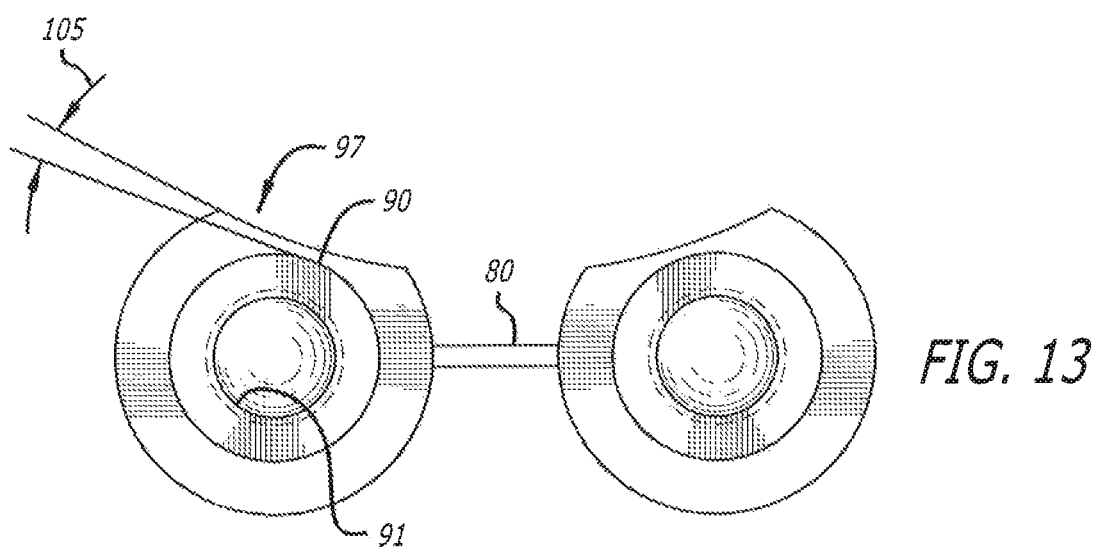
FIG. 13 is a top view of a modification of the harness shown in FIG. 12.
Figure 14:
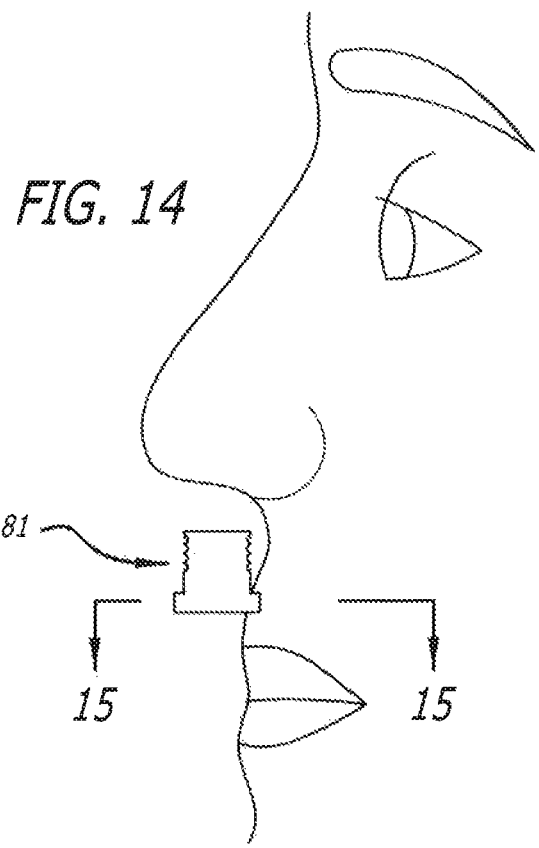
FIG. 14 is a front view, in reduced scale, of the device shown in FIG. 11 being inserted in a patient's nasal passage.

In use, the patient may insert the respective sheath barrels 35 and 37 in his or her nasal passages (FIG. 13) with the bridge strap 39 distal, and while the respective rims supported by the flanges block flow over the bodies and clear of the walls of the nasal passages. The patient then, upon exhaling, cause an airstream to flow past the four quadrants of the poppets to drag them distally and generate a pressure differential thereacross to drive the poppets to the distal ends of the housing devices shown in FIG. 2 to seat on the complementarily shaped seats 26 to restrict air passage out through the nasal passage.

We have discovered that restricting exhalation in this manner serves to, in many instances, effectively treat sleep apnea. It will be appreciated that the even distribution of air flow about the poppet in the streams at the four quadrants as dictated by the bypass across the cross section of the housing passage serves to essentially drive the ball poppet to the center of the passage so it will nest centrally on the seat 26 to partially seal. Also, with the relatively light weight of the poppet, the valve is opened and closed under the influence of even the lowest rate of flow such as might be experienced with a small child or an ailing patient with failing strength.

Upon inhaling, a partial vacuum will be generated in the passages above the lightweight poppets to lift them off the respective seats 26 and draw them proximally such that the pressure differential, combined with the drag of the airstreams flowing therepast will draw the poppets distally holding them centered in the passages to engage the tips of the stops 29, thus preventing proximal escape thereof while providing for air flow through the passages 61 (FIG. 3) for free exhaling by the patient.

It should be noted that the nasal resistance represents 50% of total airway resistance and that airway resistance changes with lung volume, but not in a linear fashion. Increasing lung volume above FRC (Functional Residual Capacity) only minimally decreases airway resistance hence my nasal CPAP will maintain adequate pressure keeping the airway passages open during the entire respiratory cycle(inspiration and expiration). In very low lung volumes R may become higher. As will be recognized by those of skill, R also depends on acceleration (inertance) and frictional factors.

As will occur to the reader, different patients inhale air at different rates, and some patients may inhale different rates of air at different times during the sleep cycle. In this regard, as the demand for greater airflow increases, the patient's lungs will seek to draw the air in with a greater force, thereby generating a greater partial vacuum in the passages 49, resulting in a greater pressure difference across the poppet 31 and increased velocity for the air flowing through the annulus between the poppet and wall of the passage, thus also increasing drag on the poppet, all combining to lift the poppet further off the seat and into the diametrically expanding passage, thereby increasing the cross section of the annulus formed between such poppet and wall of the passage to increase the volume of air flow.

With our nasal CPAP Functional Residual Capacity (FRC) is optimized during the expiratory, as well as the inspiratory cycles. This improves the Ventilation/Perfusion (dv/dt/dq/dt) relationships and therefore tends to maintain adequate oxygenation where Ventilation=Air Flow=Volume of air per unit of time=dv/dt and Perfusion=Blood Flow=Volume of capillary blood per unit of time–dq/dt. $CO_2$ elimination is not impaired by the level of CPAP generated by this device, as CPAP values at the target range do not impair levels of expired Carbon Dioxide, called end-Tidal $CO_2$(ETCO$_2$) nor does it impair the partial pressure of Carbon Dioxide in the blood($PCO_2$). $CO_2$ is eliminated prior to end-expiration (before the ball seats completely on the seat) as its removal to the atmosphere takes only a fraction of a second.

As will be appreciated by those of skill, my device is intended to present calculated resistance to air flow. Resistance is calculated as the driving pressure divided by airflow. Simply stated, if pressure is P and flow is dv/dt (flow=volume of air per unit time) then Resistance is calculated as P/dv/dt or R=driving pressure/airflow presented in units of cm $H_2O$/L/sec. Since our CPAP generates pressure in the range of 4-10 cm $H_2O$ (or between 40 and 100 mm $H_2O$) during the expiratory phase (expiration), the total pressure may be calculated by applying such pressure to a surface area with approximately 5 mm radius of nasal opening (surface area SA=3.14×5×5=78.5 mm$^2$=0.1256 SI) (square inch SI=625 mm$^2$) representing maximum 10/0.1256=79.61 mm $H_2O$/SI=0.11 PSI.

Referring to FIGS. 11-17, a further embodiment of our present invention includes a harness device, generally designated 81, formed with open-ended barrels 83 and 84 of elastic material, such as medical grade silicone. The barrels are configured with cylindrical sidewalls 85 and are formed at their bottom extremities with radially outwardly projecting rims 87 defining cylindrical wells 90 to receive the distal radial flanges of the housing bodies forming the housings for the ball valves.

Similar to the embodiment shown in FIG. 1, the barrels are formed with interior diameters 91 approximately 14 to 20% smaller than the outside diameter of the valve body housings to be stretched there over. The rims 87 are likewise undersized and typically project radially outwardly relative to the cylindrical bodies to be received over the distal flanges.

In practice the flanges and rims 87 cooperate to form a generally planar annular, proximally facing seal surface serving to, when the device is inserted in the nasal passage, seal against the distal surface of the nose forming the nasal passage to cooperate in sealing against leakage of air.

As will be appreciated by those skilled in the art, the outer, posterior extent of rims with an uninterrupted circumference exhibiting a complete circle could provide an obstacle tending to prop the distal extremities of the valve bodies anteriorly, causing the axis thereof to slope anteriorly and distally relative the axis of the respective nasal passages thus breaking the sealing effect against leakage of air through the interface between the exterior of the housing and the wall of the nasal passage. To overcome this problem, we have formed the annular posterior extent of the rims 87 with clearance notches 95, which angle laterally outwardly and posteriorly at an angle of approximately 150° relative to one another to thereby form respective obtuse angles relative to the sagittal plane. In one preferred embodiment, the notches 95 are formed by curved clearance surfaces 97, which might curve on radius of curvature of approximately 1½ inches to somewhat complement the shape of the patient's upper lip. In this configuration, the tangent to the circle defined by the radius forming the clearance surfaces 97 is spaced a distance of approximately 0.071 inches from the exterior diameter of the respective wells 90, as shown at 101 (FIG. 15).

As will be appreciated by those skilled in the art, the outer extent of the peripheries of the rims 87 could provide an obstacle tending to prop the distal extremities of the valve bodies anteriorly outwardly from the axis of the respective nasal passages and lifting the flanges and rims 87, thus breaking the seal against leakage of air. To overcome this problem, we have formed the annular exterior of the rims 87 with clearance notches 95, the tangents of which at the deepest extents of their respective arcs angle laterally outwardly and posteriorly at an angle of approximately 150° relative to one another and to form respective obtuse angles relative to the sagittal plane. In one preferred embodiment, the notches 95 are formed by clearance surfaces 97 (FIG. 15), which might curve on the radius of a curvature of approximately 1½ inches to somewhat complement the shape of the patient's upper lip. In this configuration, the tangent to the circle defined by the radius forming the clearance surfaces 97 is spaced a distance of approximately 0.071 inches from the exterior diameter of the respective wells 90, as shown at 101 (FIG. 16).

Figure 17:
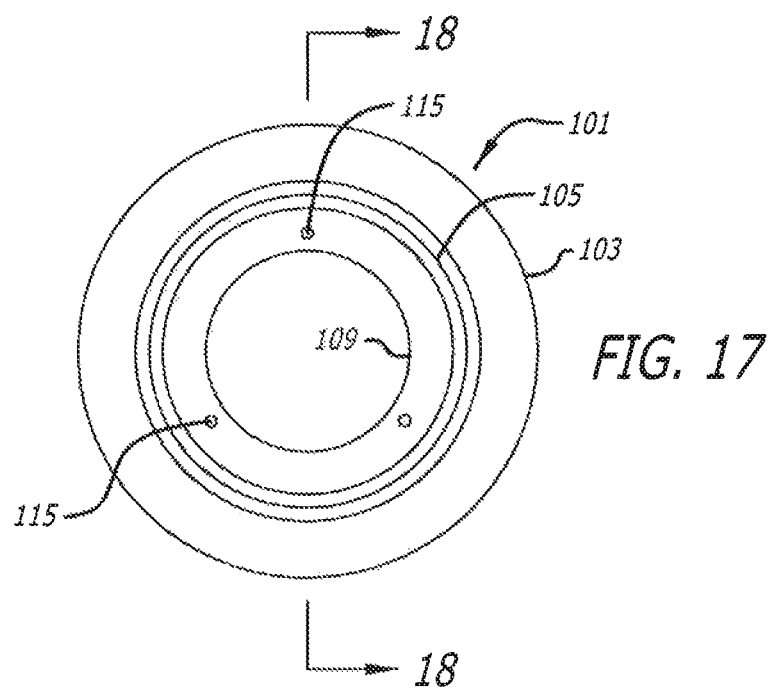
FIG. 17 is a plan view of the distal end of a further embodiment of the present invention.

In this configuration, it will be appreciated that the harness carrying the respective valve bodies can be inserted in the nasal passages shown in FIG. 17 with the clearance notches 95 providing clearance so the valve bodies are not tilted relative to the nasal passages.

Figure 15:
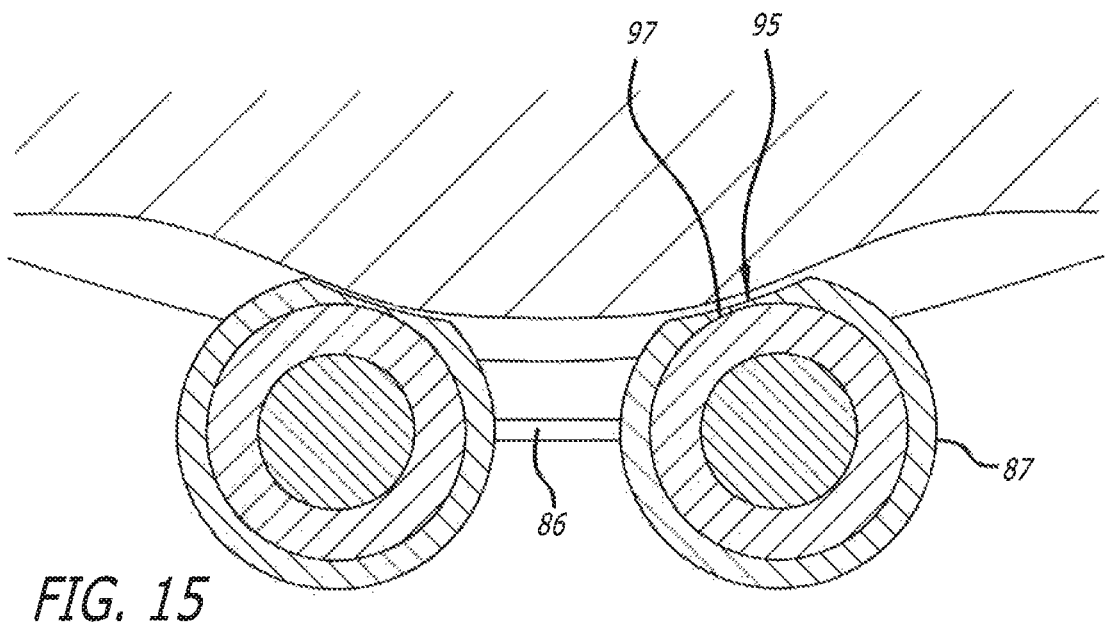
FIG. 15 is a cross sectional view, in enlarged scale, taken along the line 5-5 of FIG. 11.

As shown in FIG. 15, the bridge connector strap 86 is connected with the very distal ends of the respective rims 87 so that the distal surface thereof is disposed in a common plane with that of the distal surfaces of the rims 87 to thereby also cooperate in providing full clearance from the patient's lip for the device when inserted in the nasal passages.

Figure 16:
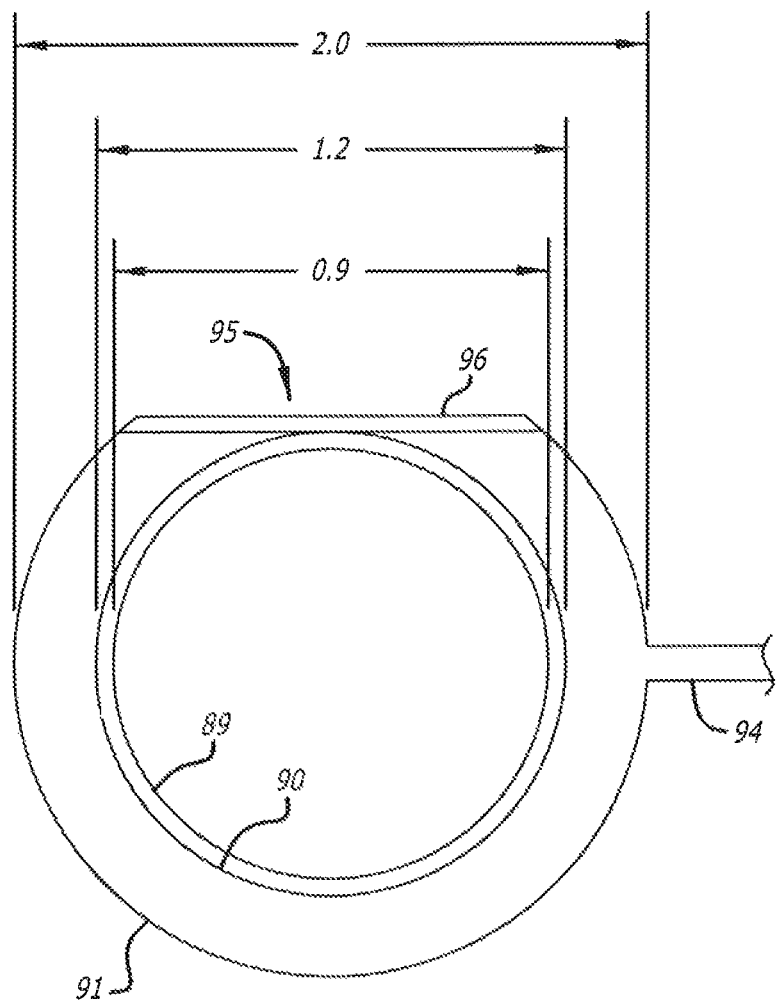
FIG. 16 is a top plan view of a further modification of a harness incorporated in the present invention.

Operation of the device of FIGS. 14-18 is similar to that of the device shown in FIG. 1 except that a selection will be made between the harness of FIG. 15 or 16 depending on the anatomy of the patient, and the valves inserted in the respective barrels 83 and 84. The barrels may then be inserted in the patient's nostril per FIG. 17, and the bridge strap 86 positioned distal of the septum of the nose itself so as to accommodate full insertion of the barrels. Experimentation has shown that the clearance notches 95 and 97 will allow for fitting of the barrels 83 and 85 and, accordingly, the valves axially into the patient's nasal passages without tiling the distal end of the barrels and valves away from the patient's lip, which could result in leakage around the barrels and/or dislodgment by or discomfort to the patient.

Referring to the modification of the harness shown in FIG. 16, the barrel 89 is formed with an interior diameter of 0.9 cm and a rim 91 is formed with an outside diameter of 2.0 cm to cooperate in forming a somewhat oversize annular sealing surface for an adult. The rim is formed with an inside diameter of substantially 1.2 cm to form a cup 90 about 0.3 cm deep for receipt of a body flange. The rim thus presents an annular sealing surface formed by an annular sealing ring having a radial dimension of 0.8 cm. In practice, this radial dimension is between 0.6 and 0.95 cm.

Projecting diametrically from the rim is a bridge strap 94. The rim is formed with a substantially planar notch 95 having a surface projecting laterally and terminating in an edge with angles proximally and anteriorly at an angle of substantially 10° to the axis of the passage to enhance clearance for the patient's lip while maintaining the sealing function against the wall of the patient's nasal passage. In operation, it will be appreciated that, when inserted, the bridge strap will tend to maintain orientation of the rim 91 relative to the patient's lip to thus maintain the notch outward to provide clearance, while the majority of the flange serves to maintain the seal at the distal end of the nasal passage.

Patients are often sensitive to blockage of their exhaling breath, something that can give them the sensation of suffocation or the like. Consequently, there is a desire to provide a sleep apnea device which blocks substantially all of the exhaling breath while leaving a very limited magnitude of exhaling flow to thereby somewhat trick the patient into having the sensation that breathing is somewhat normal to avoid the sensation of suffocation but maintaining the benefit of substantially full blockage of the exhale.

Figure 18:
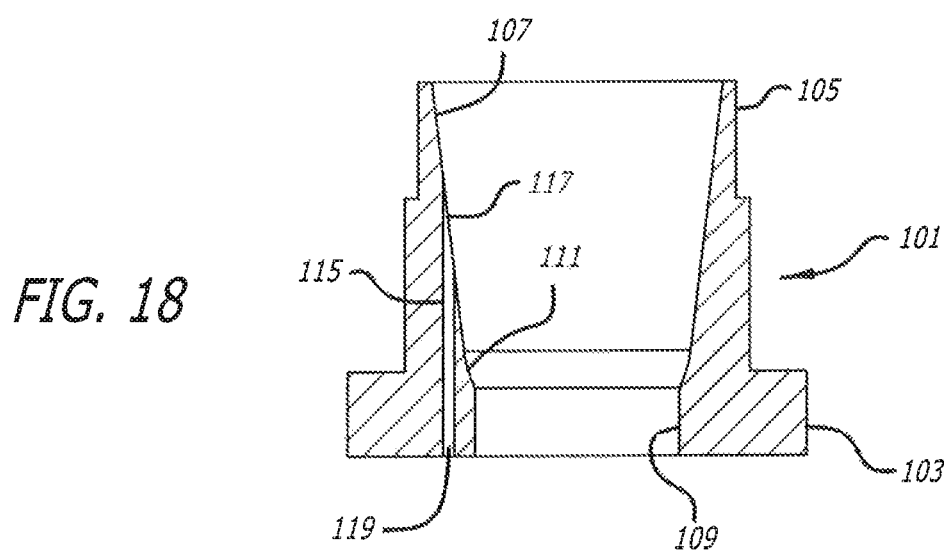
FIG. 18 is a longitudinal sectional view taken along lines 18-18 of FIG. 17.

Referring to FIGS. 17 and 18, we thus provide a tubular housing in the form of a cylindrical shell, generally designated 101, configured distally with a radially outwardly flared flange 103 and proximally with a reduced-in-diameter barrel 105 for telescopal receipt of a hat-shaped cap (not shown). In this configuration, the through interior passage 107 is conically shaped to be reduced-in-diameter distally to an inlet 109 having a diameter of 0.225 inches. Formed proximal of the inlet 109 is a valve seat 111 in the form of a sector of a sphere to complement the shape of a ball 31 to be seated thereon. Formed in the wall of the housing 101 is a bleed passage 115 having an inlet 117 proximal of the seat 113 and an outlet 119 distal of the seat such that when the ball is seated on the seat, the patient will still have the sensation of expelling air through the bleed passage 115 thus affording some degree of comfort or normalcy to diminish the sensation of suffocation.

In one preferred embodiment, we construct the housing with three bleed passages spaced equidistant about the cylindrical housing as shown in FIG. 17. Conveniently, we form the inlet 109 with a diameter of 0.225 inches and each individual passage 115 with diameters of 0.020 inches each to provide a combined length for the three diameters of 0.060 inches and an overall ratio of combined diameters to inlet diameter of substantially 0.267. We have discovered that for the dimensions mentioned, the device provides sufficient flow upon inhaling to provide oxygenation while blocking the majority of but providing for very limited flow on exhaling through the bleed passages 115 to also provide some degree of comfort.

In this preferred embodiment, the seat 111 is configured in the form of a sector of a sphere having a radius of 0.125 inches and closes to a diameter of 0.225 inches to contain a ball 0.250 inches in diameter.

In clinical tests, the sleep apnea device as described provides for excellent treatment for many patients suffering from sleep apnea. The device has been tested with numerous different patients with different anatomies and has proven effective for convenient insertion in the nasal vestibules of a typical adult patient and provides for excellent treatment of sleep apnea and comfort for the patient.

The sleep apnea device of the present invention is economical to manufacture, convenient to use, and has proven highly effective for treating sleep apnea by a mechanism comfortable for most patients to wear and use without undue hindrance of the sleep cycle.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

We claim:

1. A sleep apnea device for insertion in a patient's nasal vestibule and comprising:
    a wall forming an elongated housing for fitting in the nasal vestibule, having distal and proximal ends and formed with a through, unobstructed flow passage of a predetermined diameter leading from an inlet for flow of air and an interior, proximally facing valve seat integral with the wall;
    a ball having a diameter smaller than the predetermined diameter for seating on the seat; and
    the wall including more than two open ended bleed passages, having a diameter smaller than the predetermined diameter, leading from an inlet proximal to the seat to an outlet distal of the seat for flow of air to past the ball; whereby, when the sleep apnea device is inserted in the nasal vestibule upon the patient inhaling, inhaled flow in the flow passage will flow past the ball and upon the patient exhaling the ball will be carried into sealing engagement with the seat to block flow in the through passage and provide for air flow through the more than two bleed passages formed in the wall;
    wherein the wall is formed with the more than two bleed passages spaced equidistant thereabout bypassing the seat.

2. A sleep apnea device as set forth in claim 1 wherein: the elongated housing includes a body forming a barrel defining the through passage.

3. A sleep apnea device as set forth in claim 1 wherein: the wall is formed with a conical through passage converging distally to a reduced diameter of 0.225 inches.

4. The sleep apnea device of claim 1 wherein: each of the two or more bleed passages a diameter of 0.20 inches.

5. The sleep apnea device of claim 1 wherein: the wall includes three bleed passages.

6. The sleep apnea device of claim 1 wherein: the ball has a diameter of 0.250 inches.

7. The sleep apnea device of claim 1 wherein: the wall is configured with the through passage formed with the inlet having a diameter of 0.225 inches.

8. The sleep apnea device of claim 1 wherein: the wall is formed with the through passage having a cylindrical inlet and the ratio of the diameter of the bleed passage to the diameter of the cylindrical inlet is 0.089.

9. The sleep apnea device of claim 1 where: the wall is configured to define the through passage with a cylindrical inlet and wherein the two or more bleed passages are formed with combined diameters of a diametrical length having a ratio with the diameter of the through passage of 0.267.

10. A nasal insert for treating sleep disorders comprising:
    an elongated tubular housing for insertion in a patient's nasal passage and including a peripheral wall constructed to form a through, unobstructed flow passage for inhalation of air;
    the peripheral wall formed with a proximally facing seat disposed in the passage;
    the peripheral wall further formed with more than two longitudinal bleed passages bypassing the seat;
    a ball held captive in the passage to be carried by flow of the patient's breath upon exhaling to engage the seat and seal against flow of exhaled air through the flow passage while allowing flow through the bleed passages and to, upon inhaling, be lifted off the seat;
    wherein the wall is formed with the more than two bleed Passages spaced equidistant thereabout bypassing the seat.

11. The nasal insert of claim 10 wherein: the wall is formed with three bleed passages spaced equidistant thereabout bypassing the seat.

12. The nasal insert of claim 10 wherein: the peripheral wall forms a tubular shell, the shell being one piece.

* * * * *